US006357674B1

(12) United States Patent
Nakashima

(10) Patent No.: US 6,357,674 B1
(45) Date of Patent: Mar. 19, 2002

(54) CLEANING DEVICE FOR INTAKE PIPE PASSAGE OF ENGINE

(75) Inventor: Masao Nakashima, Ichinomiya (JP)

(73) Assignee: Hiromasa Nakashima, Aichi-ken (JP)

( * ) Notice: Subject to any disclaimer, the term of this patent is extended or adjusted under 35 U.S.C. 154(b) by 0 days.

(21) Appl. No.: 09/640,799

(22) Filed: Aug. 18, 2000

(30) Foreign Application Priority Data

Aug. 18, 1999 (JP) .......................................... 11-231229

(51) Int. Cl.[7] .......................... A61M 11/02; B05B 9/04; B05B 1/30; A62C 13/62

(52) U.S. Cl. ........................ 239/373; 239/569; 239/309

(58) Field of Search ......................... 137/624.14, 205.5, 137/564.5; 222/83, 394, 399; 239/373, 569, 309; 134/22.1–22.14, 22.17–22.19, 2, 3, 10

(56) References Cited

U.S. PATENT DOCUMENTS

| | | | | |
|---|---|---|---|---|
| 2,696,361 A | * 12/1954 | Jensen | 137/607 |
| 2,868,584 A | * 1/1959 | Faust | 239/373 |
| 3,577,808 A | * 5/1971 | Visser | 408/61 |
| 4,106,701 A | * 8/1978 | Siefken | 239/271 |
| 4,781,217 A | * 11/1988 | Rosenberg | 137/624.14 |
| 5,133,500 A | * 7/1992 | Simpson | 239/373 |
| 5,837,168 A | * 11/1998 | Rowe | 261/78.2 |

FOREIGN PATENT DOCUMENTS

| | | |
|---|---|---|
| JP | 1-262328 | 10/1989 |
| JP | 10-61456 | 3/1998 |

* cited by examiner

*Primary Examiner*—David A. Scherbel
*Assistant Examiner*—Davis Hwu
(74) *Attorney, Agent, or Firm*—Browdy and Neimark PLLC

(57) ABSTRACT

A cleaning device of an intake pipe passage of an engine provided with a container storing a washer; an air feed line with one end connected to a source of compressed air and with another end communicated with the inside of the container for feeding compressed air from the compressed air source to the inside of the container; a washer feed line with one end communicated with the inside of the container for supplying from the bottom of the container the washer compressed by the compressed air; a spray nozzle connected to the other end of the washer feed line; and a pilot valve interposed in the middle of the washer feed line and opened and closed cyclically by a cyclic pilot pressure generated by an air pulse circuit operating by air of an air source.

7 Claims, 8 Drawing Sheets

CLEANING DEVICE FOR INTAKE PIPE PASSAGE OF ENGINE

BACKGROUND OF THE INVENTION

1. Field of the Invention

The present invention relates to a cleaning device for cleaning off carbon, dust, and other dirt deposited on the inner wall of an intake pipe passage or intake tappets of an engine of an automobile etc.

2. Description of the Related Art

In general, an engine of an automobile etc., as shown schematically in FIG. 7, is comprised of a cylinder block A1 at the bottom of which is formed a crankcase A2 in which is provided a crankshaft A3. The crankshaft A2 is linked to a piston A6 provided to be able to move freely up and down in a cylinder chamber A5.

At the top of the cylinder block A1 is attached a cylinder head A10 provided with an intake tappet A7, exhaust tappet A8B and spark plug A9.

The cylinder head A10 Is connected to one end of an intake pipe passage A11. At the other end of the intake pipe passage A11 is attached an air cleaner A12. In the middle of the intake pipe passage A11 are further arranged a throttle valve A13, venturi of a carburetor A14, choke valve A15, etc.

A float chamber A16 of the carburetor A14 is designed to be fed with gasoline from a fuel tank A17 through a fuel line A18 by a fuel pump A19.

The float chamber A16 has arranged in it a not shown float valve. The float valve automatically adjusts the amount of the gasoline fed from the fuel line A18 to the float chamber A16 so that the level of the gasoline in the float chamber A16 is maintained constant at all times.

Note that excess gasoline fed into the float chamber A16 by the fuel pump A19 is returned to the fuel tank A17 by a return line A20.

Further, the cylinder head A10 has connected to it one end of an exhaust pipe passage A21. In the middle of the exhaust pipe passage A21 is provided a catalytic converter A22 for breaking down the NOx etc. in the exhaust gas. At the other end is attached an exhaust muffler A23 for muffling the sound of the exhaust.

In an engine configured as explained above, in the process of the exhaust tappet A8 closing, the intake tappet A7 opening, and the piston A6 descending, outside air flows through the intake pipe passage A11 through the air cleaner A12 and passes through the venturi of the carburetor A14. The increase in flow rate at this time causes a negative pressure by which the gasoline in the float chamber A16 is sucked out and sprayed into the intake air passage A11 as a mist.

The resultant air-fuel mixture of the gasoline and air flows into the cylinder A5 by the further descent of the piston A6.

Next, when the piston A6 rises in a state with both of the intake tappet A7 and the exhaust tappet A8 closed, the air-fuel mixture in the cylinder chamber A5 is compressed. When the piston A6 reaches close to top dead center, the spark plug A9 is charged and the air-fuel mixture in the combustion chamber A5 is ignited.

The explosive combustion of the air-fuel mixture causes the pressure in the combustion chamber A5 to sharply rise. As a result, the piston A6 is pushed down and a rotational force is caused at the crankshaft A3 through a connecting rod A4.

Next, the piston A6 again rises. In the process, when the exhaust tappet A8 is opened, the combustion gas in the combustion chamber A5 is exhausted from the exhaust pipe passage A21 to the outside of the engine.

If the engine is used for a long time in this way, carbon, dust, etc. deposit and accumulate inside the intake pipe passage A11 and at the intake tappet A7 and become a cause impairing the smooth operation of the throttle valve A13 or intake tappet A7 etc. and reducing the intake efficiency.

Therefore, in the past, as shown in FIG. 8, the fuel line A18 has been directly connected to the return line A20 connecting to the fuel tank A17 without connecting the fuel line A18 to the float chamber A16 and a feed line A25 and return line A26 of a separately prepared cleaning device 24 have been connected to the float chamber A16 for cleaning operation of the intake pipe passage A11.

The cleaning device A24 is provided with a tank A2 in which a mixture of a washer and gasoline is stored, a pump A28 for pumping the mixture in the tank A27 into the float chamber A16, a throttle valve A29 for adjusting the flow rate of the mixture, a manometer A30 for displaying the pressure of the mixture in the feed line A25, etc. and supplies the mixture in the tank into the float chamber A16 by the pump A28.

When the engine is run with the cleaning device A24 attached to the float chamber A16, the float chamber A16 is supplied with the mixture of the washer and gasoline instead of gasoline and the mixture sprayed as a mist from the venturi of the carburetor A14 to the intake pipe passage A11.

While the mist or gasified mixture passes through the inside of the intake pipe passage A11 or intake tappet A7, the washer contained in the mixture removes the carbon, dust, and other dirt deposited on the inside wall of the intake pipe passage A11 or intake tappet A7 and flushes it into the cylinder chamber A5.

There, the gas of the mixture and the carbon, dust, etc. entrained in it are burned by the ignition of the spark plug The combustion gas is exhausted from the exhaust tappet through the exhaust pipe passage to the outside as exhaust gas.

As another method of cleaning an intake system of an automobile engine, for example, as disclosed in Japanese Unexamined Patent Publication (Kokai) No. 10-61456, there is known the method of cleaning an intake system by using a special nozzle to inject and spray a washer inside the throttle chamber of an automobile engine equipped with an electronically controlled fuel injection system.

In a first aspect of the method of cleaning disclosed in Japanese Unexamined Patent Publication (Kokai) No. 10-61456, a blowby hose connected to the connection line of the air duct is detached and instead a special nozzle is set through a plug comprised of silicone rubber etc. connected to a tube leading to a washer container. The washer is injected and sprayed into the throttle chamber from an injection port of the nozzle.

In a second aspect of the method of cleaning disclosed in Japanese Unexamined Patent Publication (Kokai) No. 10-61456, the top lid of an air cleaner of an engine provided with a throttle chamber with a built-in air flow meter directly below the air cleaner is detached and a special nozzle used to inject and spray a washer inside the throttle chamber from a position past the air flow meter through a mesh at the top of the air flow meter.

In both the method of the first and second aspects explained above, the washer is injected and sprayed into the throttle chamber while running the engine. The engine is continued to run idle after spraying until there is no longer any smoke, that is, the washer remaining in the engine has been all burned, and the cleaning operation then ended.

Summarizing the problems to be solved by the present invention, in the cleaning device A24 of the related art shown in FIG. 8, since the work of cleaning the intake pipe passage A11 included the step of detaching the gas line A18 and return line A20 connecting the float chamber A16 of the carburetor A14 and the fuel tank A17 and connecting the fuel line A25 and return line A26 of the cleaning device A24 to the float chamber A16, special facilities for the cleaning work and specialized skills were required. General users therefore could not do the cleaning work by themselves.

On the other hand, with the cleaning methods disclosed in Japanese Unexamined Patent Publication (Kokai) No. 10-61456, an aerosol can was used for the washer container. With diesel engines or the recent high compression ratio gasoline engines, however, there was the danger of the propane propellant filled inside the aerosol can for spraying the washer spontaneously igniting and exploding when the temperature inside the cylinder chamber rose in the process of the compression stroke of the piston and the excessive pressure caused at that time causing the connecting rod etc. to bend.

SUMMARY OF THE INVENTION

An object of the present invention is to provide a cleaning device which solves the above problems of the related art and enables the easy, safe cleaning of the intake pipe passage of various types of engines Without requiring special facilities or skills.

According to the present invention, there is provided a cleaning device of an intake pipe passage of an engine comprising a container storing a washer; an air feed line with one end connected to a source of compressed air and with another end communicated with the inside of the container for feeding compressed air from the compressed air source to the inside of the container; a washer feed line with one end communicated with the inside of the container for supplying from the bottom of the container the washer compressed by the compressed air; a spray nozzle connected to the other end of the washer feed line; and a pilot valve interposed in the middle of the washer feed line and opened and closed cyclically by a cyclic pilot pressure generated by an air pulse circuit operating by air of an air source.

Preferably, further provision is made of a container holder having a holding face provided with a seal member for sealing the area around the bottom end of the container filled with the washer, a clamp member for bringing the area around the bottom end face in close contact with the seal member and clamping the container to the holding face, and a cutter provided to be able to be projected and retracted from the holding face at the inner circumference of the seal member for breaking through the bottom end of the container clamped on the holding face at the projecting position to form an opening; the air feed line and washer feed line are connected to the container holder, compressed air of the air feed line Is introduced from the opening of the container formed by the cutter into the container, and that compressed air is used to send the washer in the container through the opening from the washer feed line toward the spray nozzle.

More preferably, the spray nozzle is comprised of a nozzle body for spraying the washer and a nozzle holder provided with a plurality of readily elastically deformable support legs flared outward radially in one direction from the axial direction of the nozzle body, and the nozzle holder can be attached to or detached from the nozzle body selectively from the direction where the front ends of the support legs flare to the front outward past the front end of the nozzle body and the direction where they flare outward to the rear of the nozzle body.

BRIEF DESCRIPTION OF THE DRAWINGS

These and other objects and features of the present invention will become clearer from the following description of the preferred embodiments given with reference to the attached drawings, in which:

FIG. 5 is a view of an example of a cleaning device of an intake pipe passage of the related art.

DESCRIPTION OF THE PREFERRED EMBODIMENTS

Preferred embodiments of the present invention will be described next with reference to the attached drawings.

The cleaning device of an intake pipe passage of an engine uses compressed air supplied through an air feed line from a compressed air source comprised of an air compressor or accumulator to as to eject a washer stored in a container through a washer feed line and spray it from a spray nozzle connected to an end of the washer feed line to the inside of the engine intake pipe passage.

The washer is sprayed into the intake pipe passage while the engine is running. The washer penetrating into the intake pipe passage removes the carbon, dust, and other dirt deposited on the walls of the intake pipe passage, intake tappet, etc.

The washer then flows into the combustion chamber of the engine along with the air-fuel mixture of the gasoline mixed with in the carburetor midway and is completely burned up. The combustion gas passes through the exhaust pipe passage and is exhausted as exhaust gas to outside the engine.

In the present invention, the washer is sprayed intermittently from the spray nozzle using a pilot valve cyclically controlled by an air pulse circuit. Therefore, it is possible to prevent feeding a large amount of washer which cannot be burned up in the combustion chamber into the intake pipe passage and thereby prevent poor engine operation.

Further, in the present invention, it is also possible to directly connect the air feed line and washer feed line to a sealed container such as a tank filled with a washer and spray the washer in the container from the spray nozzle by compressed air. In this case. it is possible to attach a metal can or other container filled and sealed with a certain amount of the washer in advance by a clamp member to a container holder connected to the air feed line and washer feed line, break through the bottom end of the container by a cutter provided at the container holder, and feed the washer in the container from the washer feed line.

Further, by comprising the spray nozzle by a nozzle body for spraying the washer in the intake pipe passage of the engine and a nozzle holder provided with a plurality of readily elastically deformable support legs and enabling the nozzle holder to be attached to the nozzle body selectively from the direction where the front ends of the support legs flare to the front outward past the front end of the nozzle body and the direction where they flare outward to the rear of the nozzle body, it is possible to hold the spray nozzle in the air cleaner by the plurality of support legs of the nozzle holder or bend back the support legs of the nozzle holder and secure the holder to the inner wall of the intake pipe passage by their elastic force so as to position the spray nozzle inside the intake pipe passage for the cleaning work.

Figure 1:
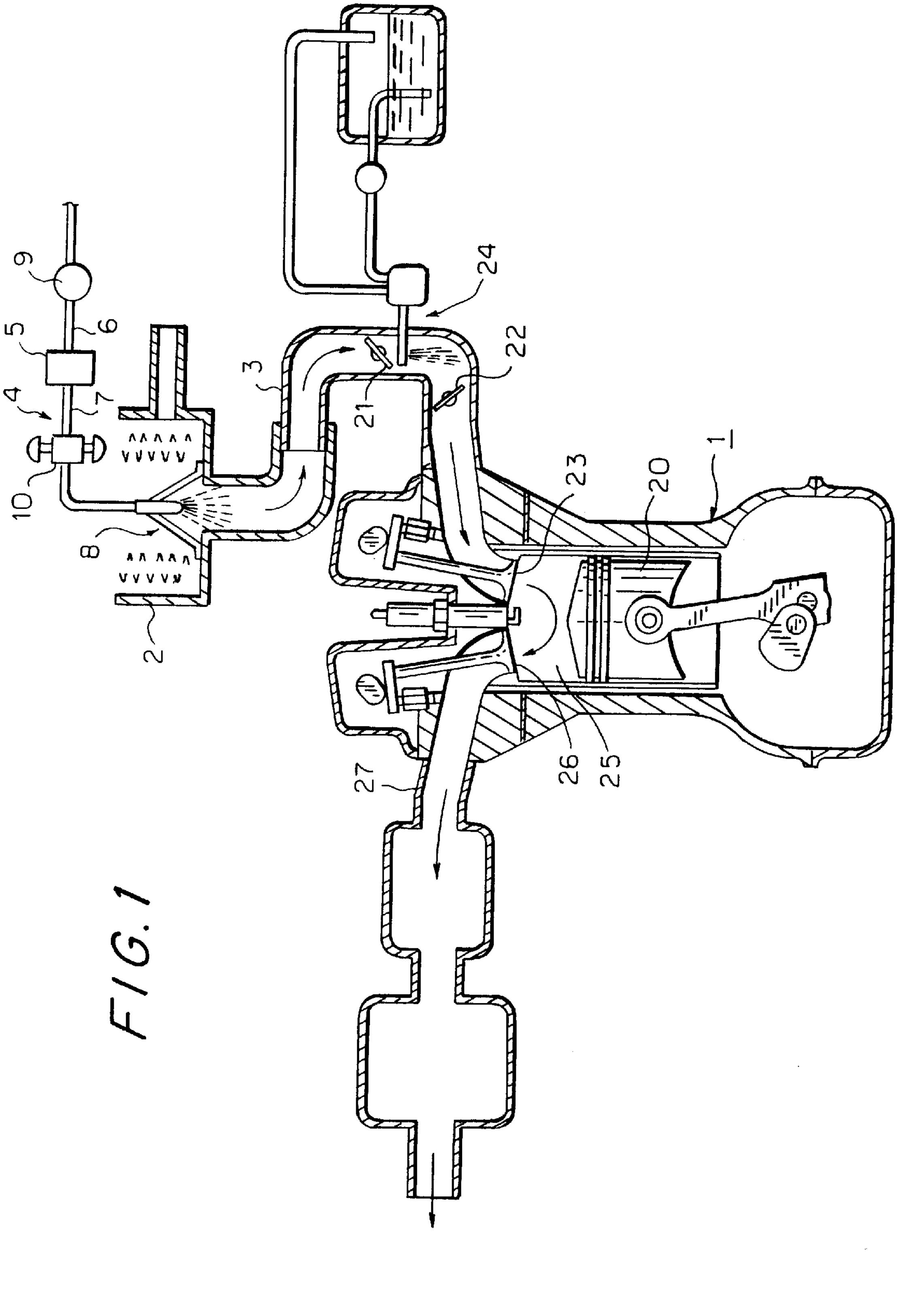
FIG. 1 is a schematic view of a cleaning device of an intake pipe passage of an engine according to a first embodiment of the present invention.

Next, specific embodiments of the present invention will be explained with reference to the drawings. FIG. 1 is a view of a cleaning device of an intake pipe passage of an engine according to a first embodiment of the present invention. In the present embodiment, the cover (not shown) of the air cleaner 2 of the engine 1 is detached and a washer sprayed from there into the intake pipe passage 3 by the cleaning device 4 for the cleaning operation.

The cleaning device 4 is provided with a container 5 storing a washer; an air feed line 6 with one end connected to a not shown source of compressed air such as an air compressor and with another end communicated with the inside of the container 5 for feeding compressed air from the compressed air source to the inside of the container 5; a washer feed line 7 with one end communicated with the inside of the container 5 for supplying from the bottom of the container 5 the washer compressed by the compressed air; and a spray nozzle 8 connected to the other end of the washer feed line 7.

Note that the washer feed line 7 is constructed so that at least the part near the spray nozzle 8 is flexible.

A pressure reducing valve 9 is provided in the middle of the air feed line 6 supplying the compressed air from the compressed air source to the container 5 and adjusts the pressure of the air introduced to the container 5 side. Further, a manually operated valve 10 is provided at a position near the spray nozzle 8 of the washer feed line 7.

Figure 2:
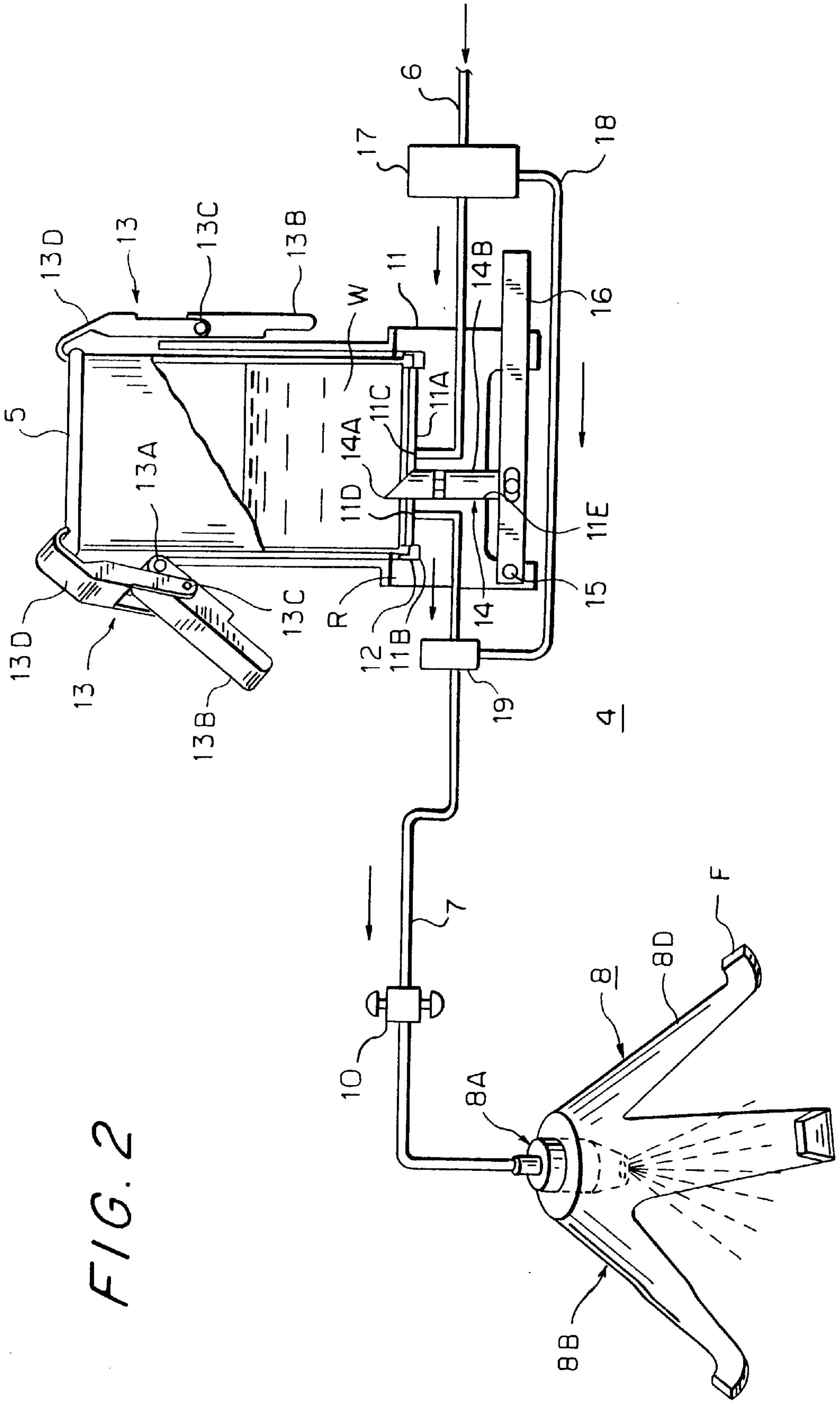
FIG. 2 is a view of the principal structure of a cleaning device of an intake pipe passage of an engine of the present invention.

FIG. 2 is a view of the principal structure of the cleaning device 4. The container 5 storing the washer is in this embodiment formed by a cylindrical metal can filled with a washer W and is used held by a container holder 11, not shown in FIG. 1.

The container holder 11 is provided with a seal member 12, for sealing the area around the bottom end of the container 5, fit into a ring-like groove 11B formed at the circumference of a holding face 11A. Note that in this embodiment, a rubber O-ring is used as the seal member 12.

The ring-shaped groove 11B is formed at an inner circumference of an engagement rim R which protects upward from the holding face 11A and engages and positions the outer circumference of the container 5.

Further, the container 5 is designed to be secured on the holding face 11A by a plurality of clamps 13 provided at the top of the container holder 11 at the position with its bottom end inserted into the engagement rim R of the container holder 11.

That is, each of these clamps 13 is comprised of a clamp lever 13B pivotally supported with respect to the container holder 11 by a clamp shaft 13A and a clamp body 13D pivotally connected to the clamp lever 13B by a connecting shaft 13C. By pressing down the clamp levers 13B, the clamp bodies 13D push the container 5 downward and press the area around the bottom end against the seal member 12 so that the space between the holding face 11A and the bottom end of the container is sealed from the outside.

On the other hand, the holding face 11A of the container holder 11 is formed with an air inlet 11C communicated with the air feed line 6 and a washer outlet 11D communicated with the washer feed line 7.

Further, the container holder 11 is provided with a cutter 14 held to be slidable in the vertical direction so that its top end can project from or retract into the holding face 11A. The top end of the cutter 14 is formed with a sharp cutting edge 14A. When projecting upward as shown in FIG. 2, it breaks through the bottom end of the container 5 to open it.

Below the cutting edge 14A of the cutter 14 is connected a circular section shaft 14B. The shaft 14B is slidably guided and supported in a support hole 11E formed in the container holder 11.

Note that while not shown in detail, the washer is prevented from leaking downward from the container holder 11 through the clearance between the shaft 14B and the support hole 11E by liquid-tightly sealing the clearance between the support hole 11E and the shaft 14B of the cutter 14 by an O-ring.

The bottom end of the shaft 14B is attached to a portion in the middle of a container opening lever 16, with one end pivotally supported by a lever shaft 15, close to the lever shaft 15 in a manner able to be pivot and able to be displaced slightly in the longitudinal direction of the container opening lever 16.

Therefore, if the cutting edge 14A of the cuter 14 is made to sink into and retract from the holding face 11A of the container holder 11, a new container 5 filled with washer W Is secured to the holding face 11A by the clamps 13, and the other end of the container opening lever 16 is lifted by hand, the cutter 14 rises and the cutting edge 14A breaks through the bottom of the container to form a new opening.

If compressed air is introduced from a not shown compressed air source to the air feed line 6 in this state, the compressed air flows from air inlet 11C opened in the holding face 11A of the container holder 11 into the container 5 through the opening formed by the cutting edge 14A.

On the other hand, the washer W in the container 5 is ejected by the compressed air entering from the bottom opening and sent from the washer outlet 11D formed in the holding face 11A of the container holder 11 to the washer feed line 7. When the manually operated valve 10 is opened, it is sprayed in a mist from the spray nozzle 8.

Further, while not illustrated here, a check valve is provided in the air feed line 6 to prevent the washer in the container 5 from flowing back to the compressed air source side.

In the present embodiment, an air pulse circuit 17 is provided in the middle of the air feed line 6. The air pulse circuit 17 generates a cyclic pilot pressure in a pilot passage 18 by the flow of the compressed air passing through the air feed line 6. The end of the pilot passage 18 is connected to a pilot valve 19.

Note that the air pulse circuit 17, pilot passage 18, pilot valve 19, etc. are not shown in FIG. 1.

The pilot valve 19 is provided to cyclically interrupt. the flow of the washer in the washer feed line 7 in response to the pilot pressure cyclically supplied from the pilot passage 18. Due to this, as shown in FIG. 1, excess washer is prevented from being fed when cleaning the intake pipe passage 3 of the engine 1.

Figure 3:
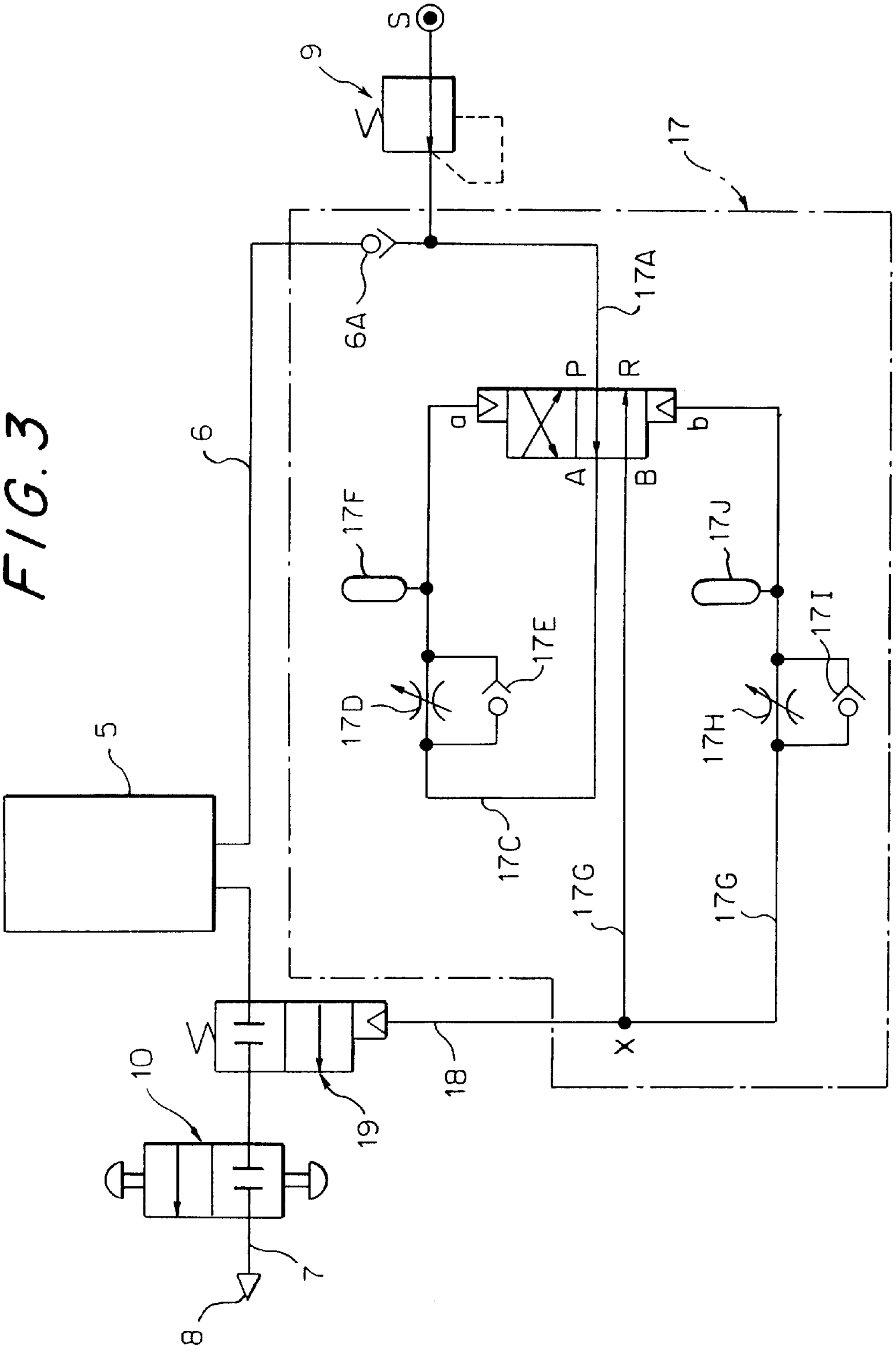
FIG. 3 is a diagram of the air circuit showing an example of an air pulse circuit used in the cleaning device of an intake pipe passage of an engine of the present invention.

FIG. 3 is a diagram of the air circuit showing an example of the air pulse circuit. The air pulse circuit 17 has a pilot directional control valve 17B with an air intake line 17A, branched from the air feed line 6 at the downstream side of the pressure reducing valve 9, connected to a port P.

Note that the air feed line 6 has a check valve 6A for preventing backflow of the washer at the downstream side of the branching position of the air intake line 17A.

A port A of the pilot directional control valve 17B is connected to the pilot passage 17C. In the middle of the pilot passage 17C are provided in parallel a variable throttle valve 17D and a check valve 17E for preventing the flow of air to the pilot port A side of the pilot directional control valve 17B. An accumulator 17F is provided between the variable throttle valve 17D and check valve 17E and the pilot port A.

On the other hand, the port B of the pilot directional control valve 17B is connected to a pilot passage 17G. The pilot passage 17G is connected to a pilot port a of the directional control valve 17B and is provided in its middle in parallel with a variable throttle valve 17H and a check valve 171 for preventing the flow of air to the pilot port B side. An accumulator 17J is provided between the variable throttle valve 17H and check valve 17I and the pilot port B.

Further, a pilot passage 18 for operating the normally closed pilot valve 19 interposed in the middle of the washer feed line 7 is branched from a position X in the middle of the pilot passage 17G.

Next, an explanation will be made of the operation of the air pulse circuit 17 comprised in this way. As shown in FIG. 3, first, the port P of the pilot directional control valve 17 is communicated with the port A and the port B is communicated with the port R open to the atmosphere.

In this state, no pressure forms in the pilot passage 17G and the pilot passage 18, therefore the pilot valve 19 is closed.

On the other hand, air gradually flows from the compressed air source S from the air introduction line 17A through the port P and port A of the pilot directional control valve 17B to the accumulator 17F.

As a result, the air pressure applied to the pilot port A of the pilot directional control valve 17B through the pilot passage 17C gradually rises. When reaching a predetermined pressure, the port P of the pilot directional control valve 17B is switched to be connected to the port B and the port R to be connected to the port A.

This being done, the air which had accumulated in the accumulator 17F is discharged through the check valve and pilot directional control valve 17B to the atmosphere and the pilot pressure which had been applied to the pilot port A disappears.

Simultaneously, the compressed air flows from the compressed air source S through the pilot directional control valve 17B to the pilot passage 17G. A part of the compressed air flows from the position X to the pilot passage 18 and opens the pilot valve 19.

At this time, if the manually operated valve 10 is opened, the washer stored in the container 5 is sprayed from the spray nozzle 8 through the washer feed line 7 by the pressure of the compressed air introduced into the container 5 through the air feed line 6.

On the other hand, the remaining portion of the compressed air which had flowed into the pilot passage 17G gradually flows through the variable throttle valve 17H to the accumulator 17J. The air pressure applied to the pilot port B of the pilot directional control valve 17B through the pilot passage 17G gradually rises. When reaching a predetermined pressure, the pilot directional control valve 17B again switches to the position shown in FIG. 3.

As a result, the air pressure in the pilot passage 18 and the pilot passage 17G is released to the atmosphere through the port R of the pilot directional control valve 17B. Along with the disappearance of the pilot pressure of the pilot passage 18, the pilot valve 19 is closed.

By cyclically repeating the above operation after this, the air pulse circuit 17 automatically cyclically operates the pilot valve 19. Note that the amount of throttling of the two variable throttle valves 17D and 17H may be adjusted to adjust the operating cycle of the pilot valve 19 or the ratio of time the valve is closed and the time the valve is open.

Next, an explanation will be made of the spray nozzle 8 used for the cleaning device of the present invention. The spray nozzle 8, as shown in FIGS. 4A and 4B, is comprised of a nozzle holder 8A connected to the end of the washer feed line 7 for spraying from its front end a mist of the washer sent by pressure through the washer feed line 7 and a nozzle holder 8B fit around and secured to the outer circumference of the nozzle body 8A in an attachable and detachable manner.

The nozzle holder 8B is made of rubber or a plastic and is comprised of a boss portion 8C and a plurality of readily elastically deformable support legs 8D. These support legs 8D are provided integrally around the boss portion 8C in a manner flared outward radially in one direction from the axial direction of the nozzle body 8A.

Figure 4A:
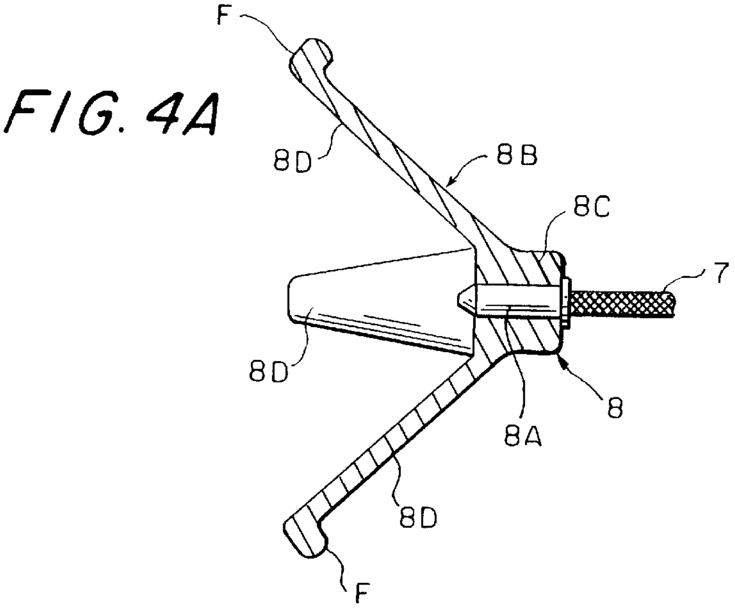
FIGS. 4A to 4C are views of the structure of a spray nozzle used in the cleaning device of an intake pipe passage of an engine of the present invention.
Figure 4B:
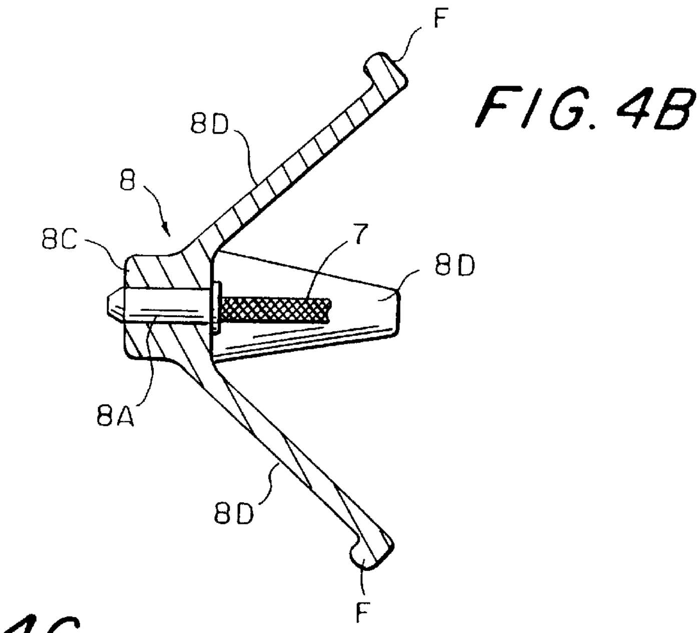
Figure 4C:
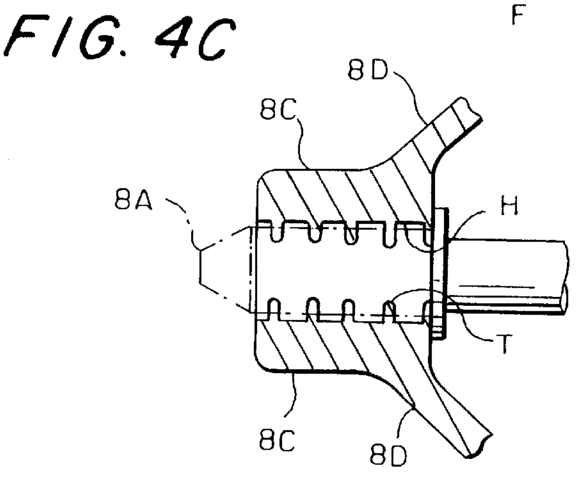

As shown in FIG. 4C, the boss portion 8C is formed with a through hole H formed inside with a plurality of ring-shaped projections T. When the nozzle body 8A is inserted into the through hole H, the nozzle holder 8B is secured and held by the nozzle body 8A by the friction between the projections T and the outer circumferential surface of the nozzle body 8A.

As shown in FIG. 4A, the nozzle holder 8B can be attached to or detached from the nozzle body selectively from the direction where the front ends of the support legs 8D flare to the front outward past the front end of the nozzle body 8A and, as shown in FIG. 4B, the direction where they flare outward to the rear of the nozzle body 8A. Further, the front ends of the support legs 8D of the nozzle holder 8B are formed with hooks F for engaging with the opening of the intake pipe passage of the engine.

Next, an explanation will be made of the routine for the work of cleaning the inside of the intake pipe passage 3 from the position of the air cleaner 2 of the engine 1 shown in FIG. 1 using the cleaning device 4 comprised as explained above.

In this case, the spray nozzle 8 is put together with the nozzle holder 8B attached to the nozzle body 8A in the direction shown in FIG. 4A. The spray nozzle 8 is arranged facing vertically downward in the air cleaner 2 using the plurality of support legs 8B of the nozzle holder 8A so that the spray port (not shown) faces the intake pipe passage 3 opened at the center of the bottom of the air cleaner 2 from which the cover has been removed.

Next, the washer in the container 5 is supplied to the washer feed line 7 by the compressed air sent from the compressed air source to the air feed line 6 in the state with the engine 1 running. When the manually operated valve 10 is then opened, the washer is sprayed from the spray port formed at the front end of the nozzle body 8A to the Inside of the intake pipe passage 3.

The washer thus sprayed toward the inside of the intake pipe passage 3 is sucked into the intake pipe passage 3 in the intake stroke of the piston 20 of the engine 1 and removes the carbon, dust, and other dirt deposited on the wall of the intake pipe passage 3, the choke valve 21, the throttle valve 22, the intake tappet, etc. Further, the mist-like washer sucked into the intake pipe passage 3 is mixed with the air-fuel mixture of the gasoline sprayed from the venturi of the carburetor midway and flows into the combustion chamber 25.

There, the washer containing the dirt is explosively burned together with the air-fuel mixture of the gasoline. The combustion gas is exhausted from the exhaust tappet 26 through the intake pipe passage 27 to the outside.

At this time, the washer is made to be intermittently sprayed inside the intake pipe passage 3 to prevent excess washer from being supplied into the combustion chambers.

When the cleaning work ends, the manually operated valve 10 of the cleaning device 4 is closed, then the engine 1 is left idling for a while so that the washer remaining in the intake pipe passage 3 is completely burned in the combustion chamber 25.

Figure 5:
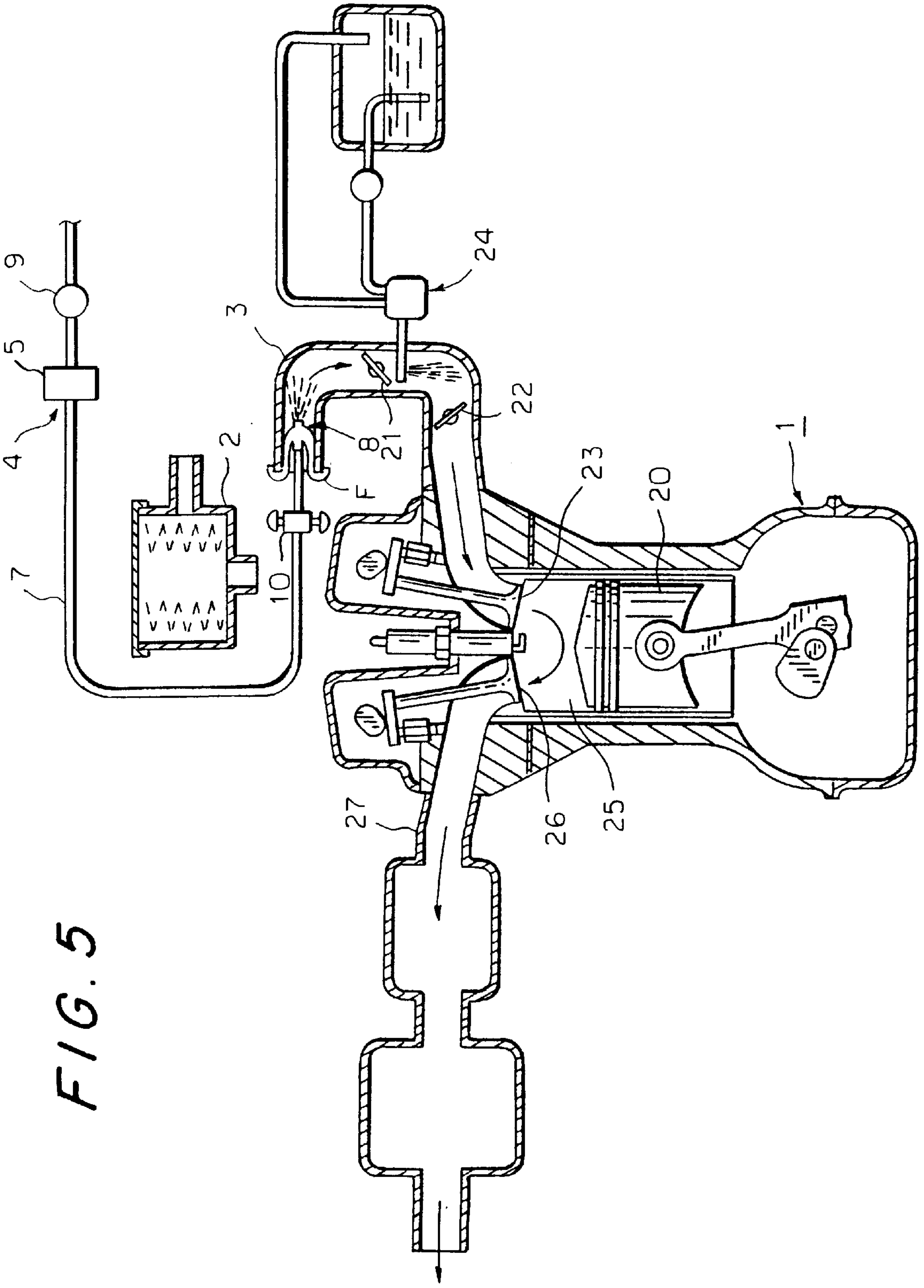
FIG. 5 is a schematic view of a cleaning device of an intake pipe passage of an engine according to a second embodiment of the present invention.

Next, FIG. 5 shows a cleaning device of an intake pipe passage according to a second embodiment of the present invention. The cleaning device 4 itself is the same as that used in the first embodiment explained above. In this embodiment, the air cleaner 2 is detached from the intake pipe passage 3 and the spray nozzle 8 directly inserted into the opening of the intake pipe passage 3 for the cleaning work. This method is used when the inside of the air cleaner 2 does not allow the spray nozzle 8 to be properly positioned.

In this case, the spray nozzle 8 is put together with the nozzle holder 8B attached to the nozzle body 8 in the direction shown in FIG. 4B. The support legs 8D are bent back using their elasticity and the spray nozzle 8 pushed inside the intake pipe passage 3 until the hooks F engage with the opening of the intake pipe passage 3 and thereby the spray nozzle 8 is secured and held by the intake pipe passage 3. Note that the cleaning work itself can be performed by a similar routine as the embodiment explained above.

Figure 6:
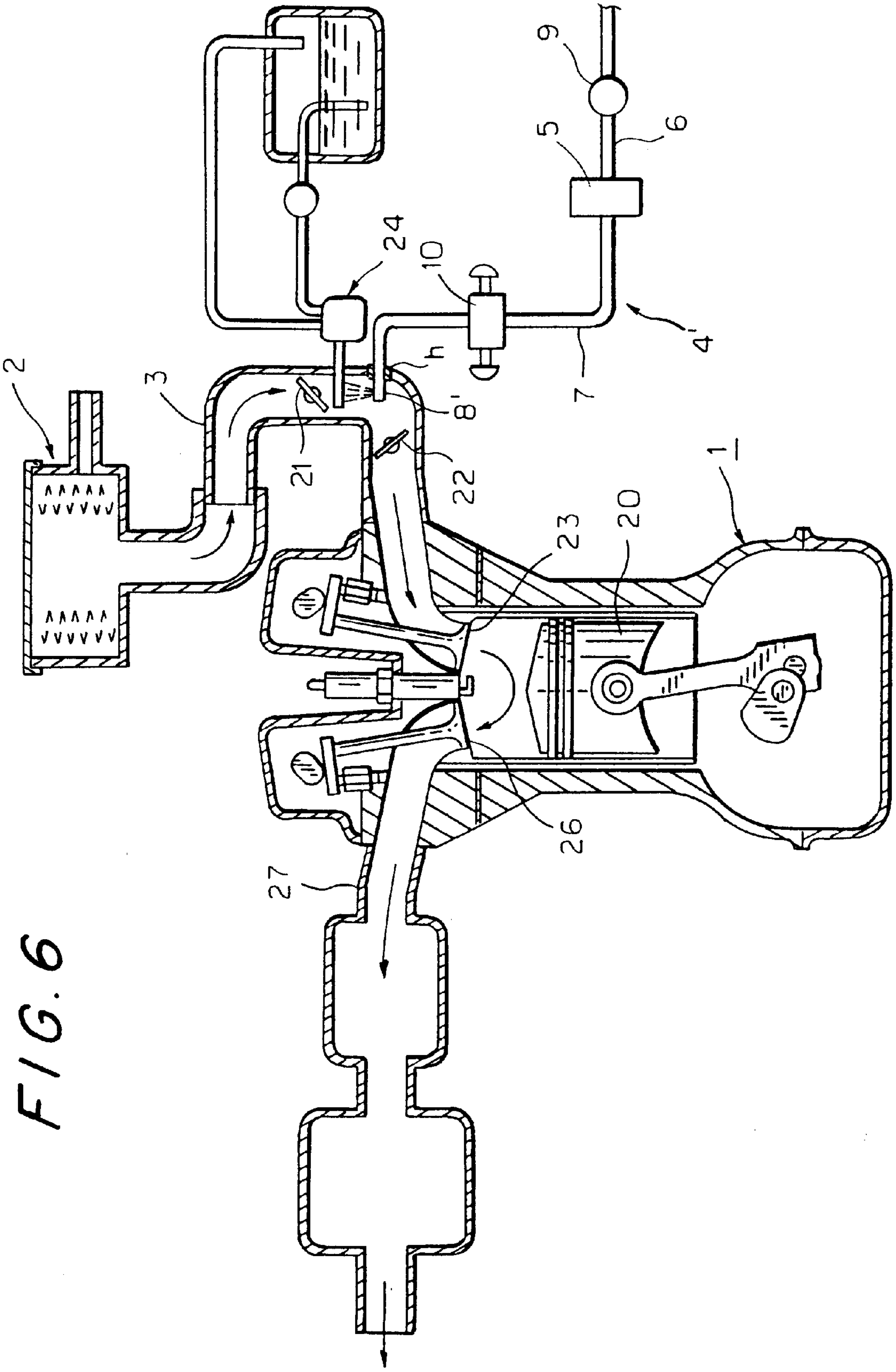
FIG. 6 is a schematic view of a cleaning device of an intake pipe passage of an engine according to a third embodiment of the present invention.
Figure 7:
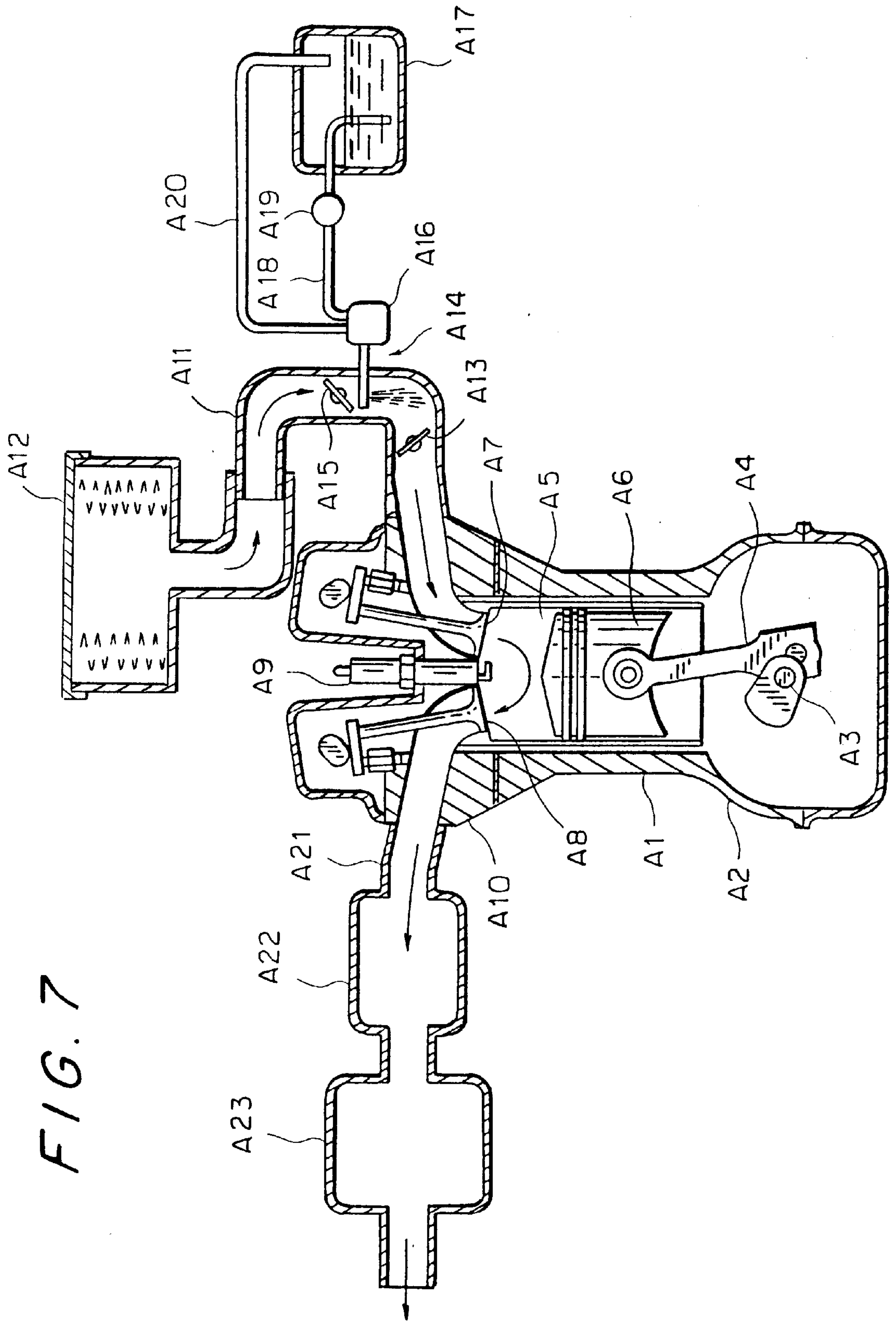
FIG. 7 is a view of the general structure of a general engine.
Figure 8:
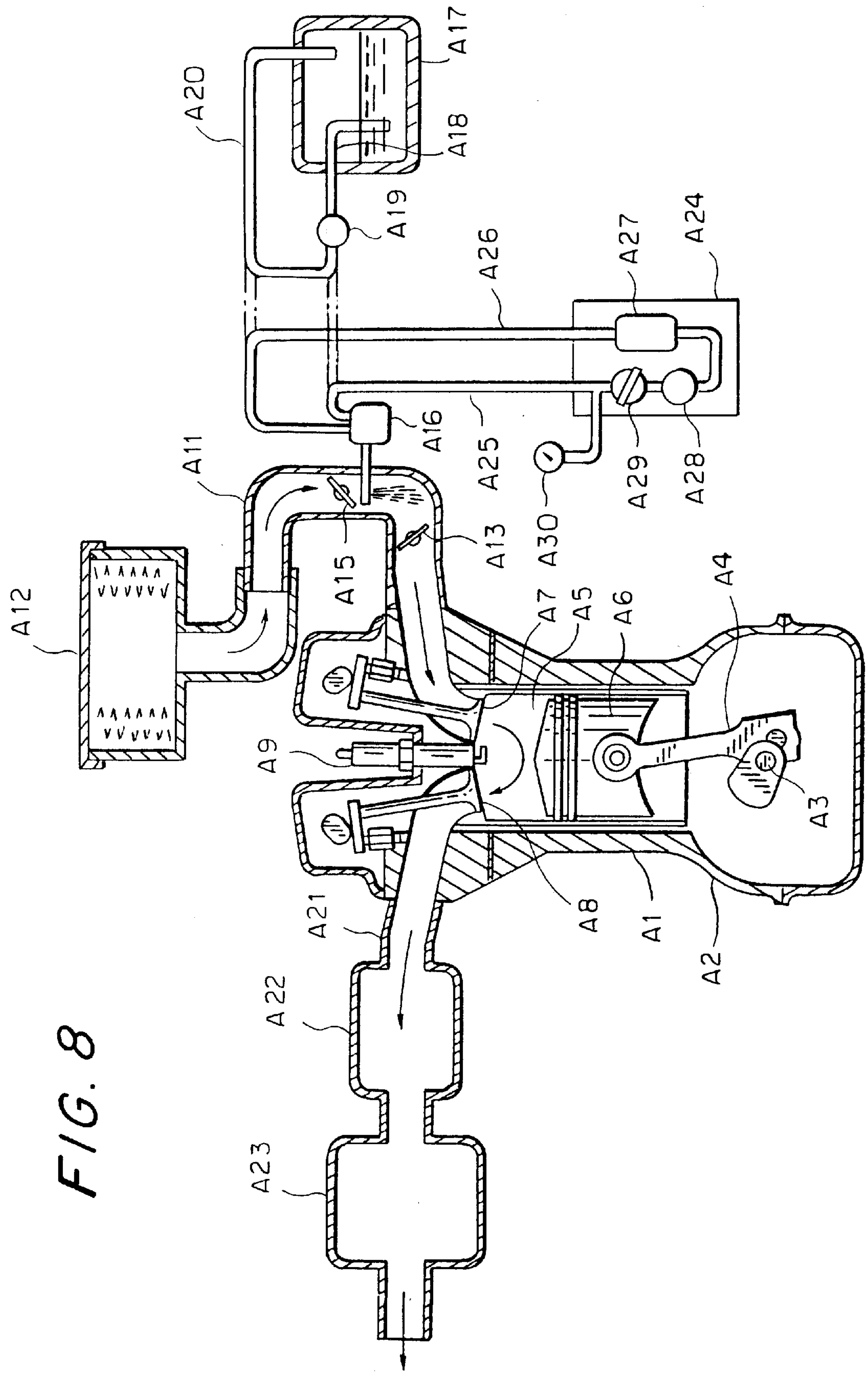

Further, FIG. 6 shows a cleaning device of an intake pipe passage according to a third embodiment of the present invention. In this embodiment, use is made of a cleaning device 4' different from the cleaning device 4 used in the above embodiments in the point of the spray nozzle 8'.

The spray nozzle 8' is connected to an end of the washer feed line 7, formed into a cylinder of substantially the same diameter as the washer feed line 7, and having the spray port of the washer formed as part of its outer circumference so as to enable the washer to be sprayed in a direction perpendicular to the longitudinal direction of the washer feed line 7.

In this embodiment, the spray nozzle 8' is used inserted into the intake pipe passage 3 from a vacuum port h formed at the wall of the intake pipe passage 3 between the venturi of the carburetor 24 and the throttle valve 22.

Note that the vacuum port h is provided for detecting the degree of vacuum in the intake pipe passage when determining the amount of power assist of the power steering system.

Further, while not shown in FIG. 6, a plug-like seal member is provided at the outer circumference of the portion of the spray nozzle 8' passing through the vacuum port h so as to fit into the inner circumference of the vacuum port h and secure the spray nozzle 8' and simultaneously seal the clearance between the vacuum port h and the spray nozzle 8'.

The spray port of the spray nozzle 8' is oriented toward the venturi side of the carburetor 24, so it is possible to effectively clean the venturi where the area of the intake passage is reduced and dirt easily accumulates. Note that in this embodiment as well, the cleaning work itself may be performed by a similar routine as the previously explained two embodiments.

In the above embodiments, the cleaning devices 4 and 4' used the air pulse circuit 17 shown in FIG. 2 and the pilot valve 19 controlled by this, but the cleaning devices may be configured without these as well.

Further, the air pulse circuit itself is not limited to the configuration shown in FIG. 3. It need only be one having the function of cyclically operating the pilot valve interposed in the washer feed line.

Further, in the above embodiments, a metal can filled and sealed with a washer was used as the container 5 and this was held and used by the container holder 11, but it is also possible to use a standing tank storing the washer as the container and directly connect the air feed line and the washer feed line to the tank.

Further, the spray nozzle is not limited to those of the embodiments explained above. It need only be structured to enable the washer to be sprayed into the intake pipe passage.

Summarizing the advantageous effects of the invention, as explained above, according to the aspect of the invention set forth in claim 1, when cleaning the intake pipe passage of the engine, the work of detaching the fuel line and return line connecting the float chamber of the carburetor and fuel tank and connecting the feed line and return line of the cleaning device to the float chamber like in cleaning work of the past is no longer necessary and no special facilities or specialized skills are required for the cleaning work, so the cleaning work can be performed easily.

Further, since the washer is sprayed into the intake pipe passage by compressed air, there is no mixture of propane and other ignitable gases such as when spraying a washer contained in a spray can into the intake pipe passage for the cleaning work, so the device can be safely used even with high compression ratio diesel engines or the recent fuel injection type gasoline engines.

Further, since an air pulse circuit is used to cyclically operate the pilot valve and thereby intermittently spray the washer into the intake pipe passage of the engine, it is possible to prevent a large amount of washer which cannot be completely burned up in the combustion chamber from being fed into the intake pipe passage and therefore prevent poor engine operation.

According to the aspect of the invention set forth in claim 2, since a metal can or other container sealed with the necessary amount of washer can be attached to a container holder for the cleaning work, the storage and handling of the washer become easy.

According to the aspect of the invention set forth in claim 3, since it is possible to hold the spray nozzle in the air cleaner by the plurality of support legs of the nozzle holder or position the spray nozzle in the intake pipe passage by bending back the support legs of the nozzle holder and securing the nozzle to the walls of the intake pipe passage by their elastic force, it is possible to select the position of the spray nozzle in accordance with the structure of the air cleaner or intake pipe passage.

While the invention has been described with reference to specific embodiment chosen for purpose of illustration, it should be apparent that numerous modifications could be made thereto by those skilled in the art without departing from the basic concept and scope of the invention.

What is claimed is:

1. A cleaning device of an intake pipe passage of an engine comprising:

a container storing a washer;

an air feed line with one end connected to a source of compressed air and with another end communicated with the inside of the container for feeding compressed air from the compressed air source to the inside of the container;

a washer feed line with one end communicated with the inside of the container for supplying from the bottom of the container the washer compressed by the compressed air;

a spray nozzle connected to the other end of the washer feed line; and a pilot valve interposed in the middle of the washer feed line and opened and closed cyclically by a cyclic pilot pressure generated by an air pulse circuit operating by air of an air source.

2. A cleaning device of an intake pipe passage of an engine as set forth in claim 1, wherein further provision is made of a container holder having a holding face provided with a seal member for sealing the area around the bottom end of the container filled with the washer, a clamp member for bringing the area around the bottom end face in close contact with the seal member and clamping the container to the holding face, and a cutter provided to be able to be projected and retracted from the holding face at the inner circumference of the seal member for breaking through the bottom end of the container clamped on the holding face at the projecting position to form an opening;

the air feed line and washer feed line are connected to the container holder, compressed air of the air feed line is introduced from the opening of the container formed by the cutter into the container, and that compressed air is used to send the washer in the container through the opening from the washer feed line toward the spray nozzle.

3. A cleaning device of an intake pipe passage of an engine as set forth in claim 1, wherein:

the spray nozzle is comprised of a nozzle body for spraying the washer and a nozzle holder provided with a plurality of readily elastically deformable support legs flared outward radially in one direction from the axial direction of the nozzle body and the nozzle holder can be attached to or detached from the nozzle body selectively from the direction where the front ends of the support legs flare to the front outward past the front end of the nozzle body and the direction where they flare outward to the rear of the nozzle body.

4. A cleaning device of an intake pipe passage of an engine as set forth in claim 2, wherein:

the spray nozzle is comprised of a nozzle body for spraying the washer and a nozzle holder provided with a plurality of readily elastically deformable support legs flared outward radially in one direction from the axial direction of the nozzle body and the nozzle holder can be attached to or detached from the nozzle body selectively from the direction where the front ends of the support legs flare to the front outward past the front end of the nozzle body and the direction where they flare outward to the rear of the nozzle body.

5. A cleaning device of an intake pipe passage of an engine comprising:

a container storing a washer;

an air feed line with one end connected to a source of compressed air and with another end communicated with the inside of the container for feeding compressed air from the compressed air source to the inside of the container;

a washer feed line with one end communicated with the inside of the container for supplying from the bottom of the container the washer compressed by the compressed air;

a spray nozzle connected to the other end of the washer feed line;

a pilot valve interposed in the middle of the washer feed line and opened and closed cyclically by a cyclic pilot pressure generated by an air pulse circuit operating by air of an air source;

wherein further provision is made for a container holder having a holding face provided with a seal member for sealing the area around the bottom end of the container filled with the washer, a clamp member for bringing the area around the bottom end face in close contact with the seal member and clamping the container to the holding face, and a cutter provided to be able to be projected and retracted from the holding face at the inner circumference of the seal member for breaking through the bottom end of the container clamped on the holding face at the projecting position to form an opening;

the air feed line and washer feed line are connected to the container holder, compressed air of the air feed line is introduced from the opening of the container formed by the cutter into the container, and that compressed air is used to send the washer in the container through the opening from the washer feed line toward the spray nozzle.

6. A cleaning device of an intake pipe passage of an engine as set forth in claim 5, wherein:

the spray nozzle is comprised of a nozzle body for spraying the washer and a nozzle holder provided with a plurality of readily elastically deformable support legs flared outward radially in one direction from the axial direction of the nozzle body and the nozzle holder can be attached to or detached from the nozzle body selectively from the direction where the front ends of the support legs flare to the front outward past the front end of the nozzle body and the direction where they flare outward to the rear of the nozzle body.

7. A cleaning device of an in take pipe passage of an engine as set forth in claim 5, wherein:

the spray nozzle is comprised of a nozzle body for spraying the washer and a nozzle holder provided with a plurality of readily elastically deformable support legs flared outward radially in one direction from the axial direction of the nozzle body and the nozzle holder can be attached to or detached from the nozzle body selectively from the direction where the front ends of the support legs flare to the front outward past the front end of the nozzle body and the direction where they flare outward to the rear of the nozzle body.

* * * * *